United States Patent
Own et al.

(10) Patent No.: US 8,927,932 B2
(45) Date of Patent: *Jan. 6, 2015

(54) SCANNING TRANSMISSION ELECTRON MICROSCOPY FOR IMAGING EXTENDED AREAS

(71) Applicant: Mochii, Inc., Seattle, WA (US)

(72) Inventors: Christopher Su-Yan Own, Seattle, WA (US); William Andregg, Woodside, CA (US); Michael Lee Andregg, Woodside, CA (US)

(73) Assignee: Mochii, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/071,614

(22) Filed: Nov. 4, 2013

(65) Prior Publication Data
US 2014/0054458 A1    Feb. 27, 2014

Related U.S. Application Data

(63) Continuation of application No. 13/303,121, filed on Nov. 22, 2011, now Pat. No. 8,598,527.

(51) Int. Cl.
| H01J 37/26 | (2006.01) |
| G01N 23/02 | (2006.01) |
| G01N 13/12 | (2006.01) |
| C12Q 1/68 | (2006.01) |

(52) U.S. Cl.
CPC .......... *H01J 37/261* (2013.01); *C12Q 1/6869* (2013.01); *H01J 2237/248* (2013.01); *H01J 2237/2802* (2013.01); *Y10S 430/143* (2013.01)

USPC ........... 250/311; 250/310; 250/306; 250/307; 250/492.3; 250/491.1; 430/296; 430/942

(58) Field of Classification Search
CPC .................. H01J 2237/248; H01J 2237/2802; H01J 37/261
USPC ........... 250/311, 310, 306, 307, 492.3, 491.1; 430/296, 942
See application file for complete search history.

(56) References Cited

U.S. PATENT DOCUMENTS

| 7,372,051 B2 * | 5/2008 | Tsuneta et al. ............. 250/492.3 |
| 8,598,527 B2 * | 12/2013 | Own et al. .................... 250/311 |
| 2012/0098953 A1 * | 4/2012 | Kotaki et al. .................. 348/80 |

* cited by examiner

*Primary Examiner* — Nikita Wells
(74) *Attorney, Agent, or Firm* — Mei & Mark LLP

(57) ABSTRACT

A scanning transmission electron microscope for imaging a specimen includes an electron beam source to generate an electron beam. Beam optics are provided to converge the electron beam. A stage is provided to hold a specimen in the path of the electron beam. A beam scanner scans the electron beam across the specimen. A controller may define one or more scanning areas corresponding to locations of the specimen, and control one or more of the beam scanner and stage to selectively scan the electron beam in the scanning areas. A detector is provided to detect electrons transmitted through the specimen to generate an image. The controller may generate a sub-image for each of the scanning areas, and stitch together the sub-images for the scanning areas to generate a stitched-together image. The controller may also analyze the stitched-together image to determine information regarding the specimen.

20 Claims, 10 Drawing Sheets

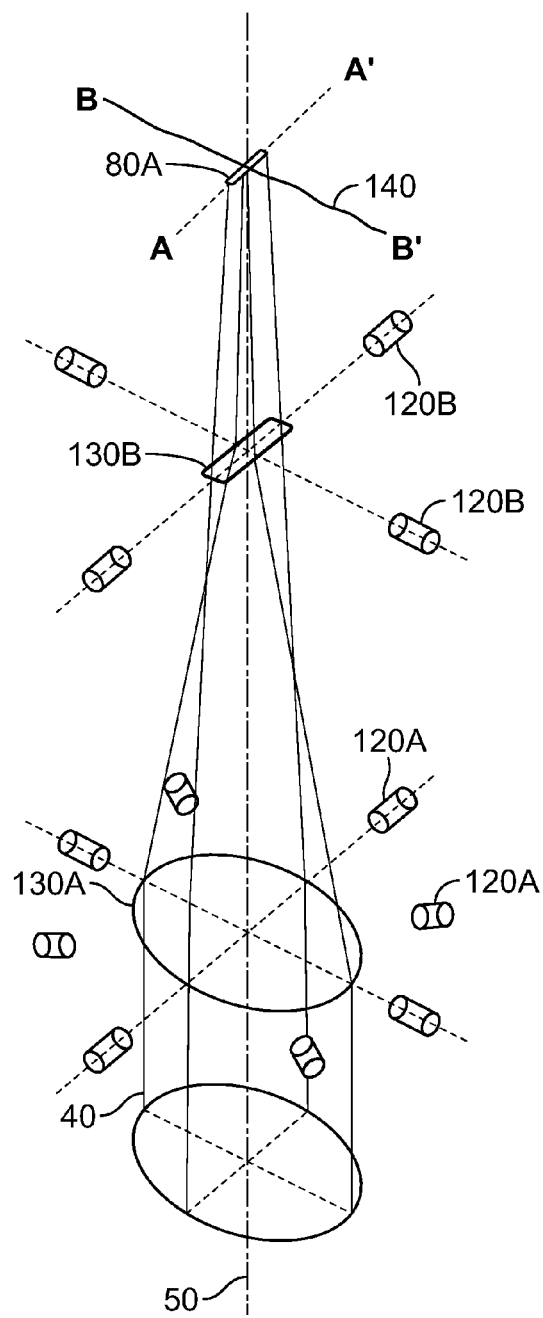
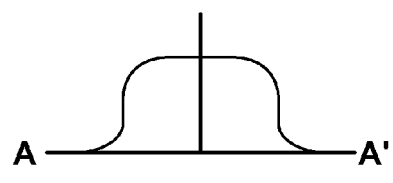
FIG. 3A
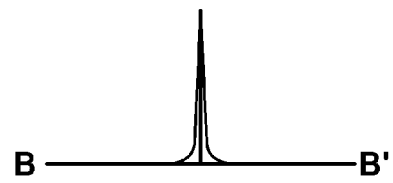
FIG. 3B
FIG. 2

SEQUENCE LISTING

<160> NUMBER OF SEQ ID NOS: 1

<210> SEQ ID NO 1
<211> LENGTH: 14
<212> TYPE: DNA
<213> ORGANISM: Homo sapiens

<400> SEQUENCE: 1
aatacggaaa tagc                                                       14

SCANNING TRANSMISSION ELECTRON MICROSCOPY FOR IMAGING EXTENDED AREAS

CLAIM FOR PRIORITY

This application is a continuation of application Ser. No. 13/303,121, filed Nov. 22, 2011, which is incorporated herein by reference in its entirety.

INCORPORATION OF SEQUENCE LISTING BY REFERENCE

This application incorporates by reference the contents of a 406 byte text file created on Jan. 19, 2012, and named "Sequence.txt," which is the sequence listing for this application.

TECHNICAL FIELD

This application relates to scanning transmission electron microscopy for imaging extended areas.

BACKGROUND

In certain applications it is desirable to use electron microscopy to sequence a polymer. Electron microscopy can theoretically be used, for example, to sequence bases of a nucleic acid, such as the bases of a strand of deoxyribonucleic acid (DNA). The polymer is labeled at its structural units and stretched onto a substrate. An electron microscope is then used to scan the polymer and thereby generate an image, which can be analyzed to identify the labels. Based on the correspondence of the label types with the structural unit types to which they bond, the polymer can be sequenced.

Using conventional transmission electron microscopy (TEM) for sequencing may, however, suffer from an undesirably low ratio of signal from the labels to noise from the substrate or other causes. Images generated by electron microscopy may also not be optimally focused at every portion of a polymer strand, which can detract from the ability to locate and identify the labels. Moreover, performing conventional transmission electron microscopy may take an undesirably long time for polymer sequencing. The throughput may be especially low for sequencing long polymers, such as a full human genome, in any practical amount of time.

Thus, it is desirable to provide electron microscopy with a signal-to-noise ratio that is sufficiently good for polymer sequencing. It is also desirable for the electron microscope images to be focused at every part of a polymer strand being examined. Moreover, it is desirable for the electron microscopy to have a substantially high throughput to sequence the polymer sufficiently fast to be practical.

SUMMARY

In one embodiment, a scanning transmission electron microscope is provided for imaging a specimen. The microscope comprises an electron beam source to generate an electron beam. The microscope has beam optics to converge the electron beam, a stage to hold a specimen in the path of the electron beam, and a beam scanner to scan the electron beam across the specimen. The microscope also has a detector to detect electrons transmitted through the specimen to generate an image. A controller is provided to (1) define one or more scanning areas corresponding to locations of the specimen, (2) control one or more of the beam scanner and stage to selectively scan the electron beam in the scanning areas, (3) generate a sub-image for each of the scanning areas, (4) stitch together the sub-images for the scanning areas to generate a stitched-together image, and (5) analyze the stitched-together image to determine information regarding the specimen.

In another embodiment, a method is provided of imaging a specimen. The method includes generating an electron beam, converging the electron beam, and holding a specimen on a stage in the path of the electron beam. The method further comprises defining one or more scanning areas corresponding to locations of the specimen, and controlling one or more of the beam scanner and the stage to selectively scan the electron beam in the scanning areas. Electrons transmitted through the specimen are detected to generate a sub-image for each of the scanning areas. The method additionally comprises stitching together the sub-images for the scanning areas to generate a stitched-together image, and analyzing the stitched-together image to determine information regarding the specimen.

In yet another embodiment, a scanning transmission electron microscope is provided for imaging a specimen. The microscope comprises an electron beam source to generate an electron beam. The microscope has beam optics to converge the electron beam into a longitudinally stretched beam, a stage to hold a specimen in the path of the electron beam, and a beam scanner to scan the electron beam across the specimen. The microscope also has a detector to detect electrons transmitted through the specimen to generate an image. A controller is provided to (1) define one or more scanning areas corresponding to locations of the specimen, (2) control one or more of the beam scanner and stage to selectively scan the electron beam in the scanning areas, (3) generate a sub-image for each of the scanning areas, (4) stitch together the sub-images for the scanning areas to generate a stitched-together image, and (5) analyze the stitched-together image to determine information regarding the specimen.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and aspects of the transmission electron microscopes described herein and, together with the description, serve to explain the principles of the invention.

FIG. 2 is a three-dimensional schematic diagram of an example of an embodiment of condenser lenses containing multipole condenser elements shaping an electron beam into a longitudinally stretched probe.

FIG. 3A is a plot of an example of the distribution of the electron beam in FIG. 2 across the A axis.

FIG. 3B is a plot of an example of the distribution of the electron beam in FIG. 2 across the B axis.

DETAILED DESCRIPTION

Figure 1:
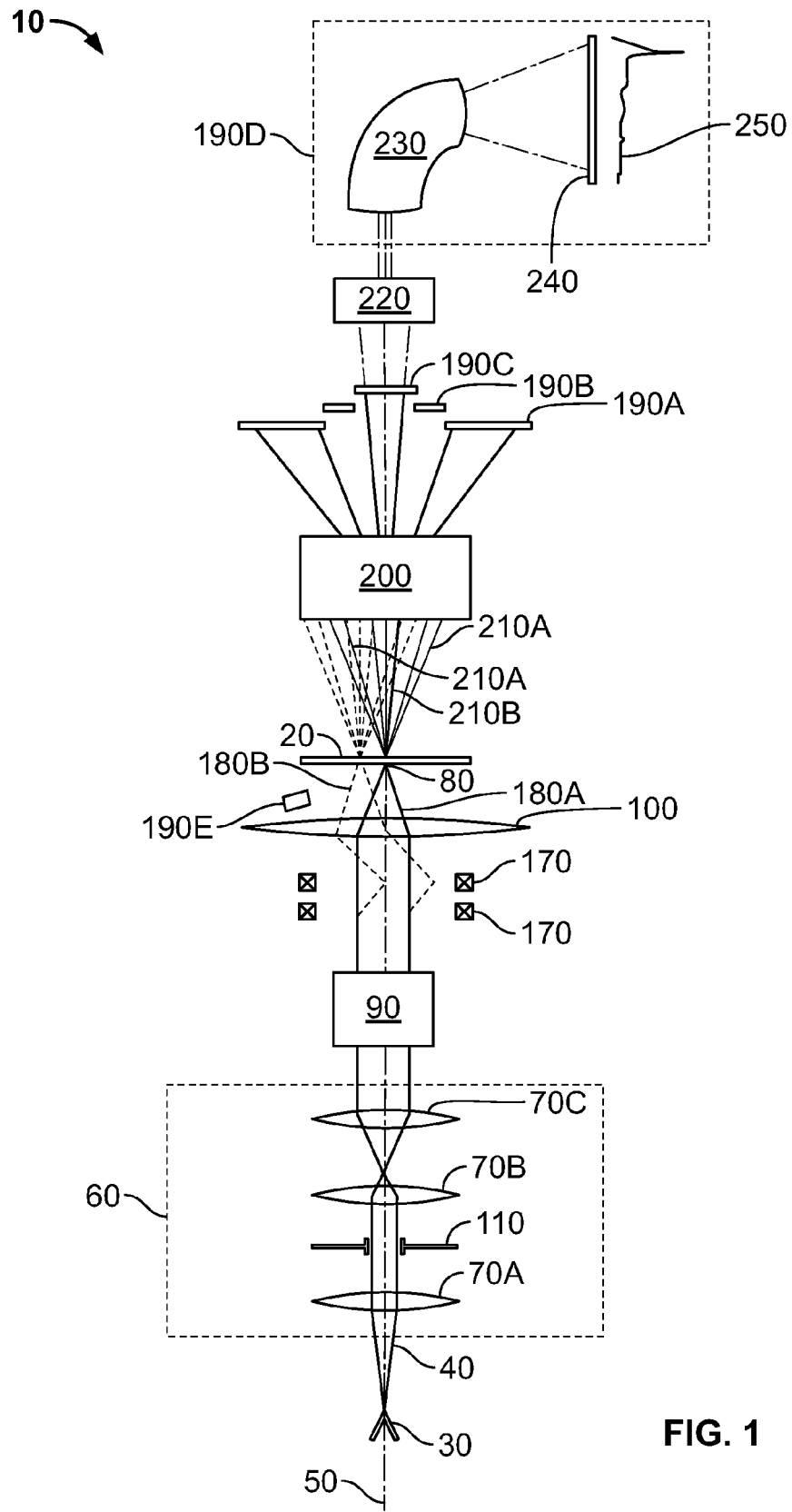
FIG. 1 is a schematic diagram of an example of an embodiment of a scanning transmission electron microscope (STEM).

A scanning transmission electron microscope (STEM) may be adapted and used advantageously to sequence polymers. The polymer may include a nucleic acid, such as for example oligonucleotides and polynucleotides, DNA, or RNA of genomic, recombinant, or synthetic origin, which may be single- or double-stranded, and represent sense or antisense strands, or any DNA-like or RNA-like material or other polymers, such as proteins, natural, recombinant, or synthetic in origin, and which may contain any nucleic acid, including variants such as 5-Metyl Cytosine and other epigenetically modified bases, artificially modified bases, and individual amino acids, both natural and artificial.

To facilitate STEM imaging of the polymer, structural units of strands of the polymer may be labeled with atoms or molecules that facilitate detection and identification. For example, the labels may be heavy atoms or clusters of atoms. Different labels may be associated with different types of structural units of the polymer, respectively. For example, each type of label may be chosen to bond selectively to a corresponding type of structural unit. Heavy atoms used for labeling may, in one version, have an atomic number of at least 55 to provide a desirable contrast during imaging. Examples of atoms that can be used for labeling include Cl, Br, I, U, Os, Pb, Au, Ag, Fe, Pt, Eu, Pd, Co, Hg, Gd, Cd, Zn, Ac, W, Mo, Mn, Rb, Cs, Ra, Ba, and Sr.

After the polymer has been labeled, it is presented for imaging in a manner suitable for obtaining images of the different labels in relation to their positions along the polymer strands. For example, the polymer strands may be stretched out on a substrate. This may involve straightening the polymer. The polymer may also be attached to the substrate, such as by bonding. The STEM sequentially scans an electron beam across the polymer, herein referred to as the sample. In this way, one or more images may be generated. These images may be evaluated, such as by a controller of the STEM, to identify the labels in relation to their location on the polymer. The identities of the labels can be used to identify the structural units of the polymer, thus sequencing the polymer.

A particularly useful application of the STEM is sequentially imaging a DNA strand in order to determine the sequence of the nucleotide base pairs of the DNA. For example, a single strand of DNA may be stretched in preparation for imaging using techniques that have been described in PCT Publication No. WO 2009/046445 dated Sep. 4, 2009, entitled "Sequencing Nucleic Acid Polymers with Electron Microscopy," and filed as International Application No. PCT/US2008/078986 on Jun. 10, 2008 (this PCT publication is hereby incorporated by reference in its entirety). A particular set of nucleotides may be labeled using a label that contains at least one heavy scatterer. Examples of such labels include osmium, triosmium, and platinum.

In the case of a double-stranded nucleic acid, such as DNA, the labels may be attached to either one strand or both strands of the nucleic acid. If only one strand is to be labeled, the sequence of the other strand may be inferred from the sequence of the imaged strand. A complementary strand, namely a second strand with nucleotides complementary to a first strand, may be formed for the purpose of labeling and imaging in lieu of the first strand. The two strands of the nucleic acid may be separated from each other by, for example, denaturing processes, such as thermal and enzymatic, that can be used to break the hydrogen bonding between the strands. Alternatively, a single strand may be synthesized from a template. For example, polymerase chain reaction (PCR) or reverse transcriptase processes may be utilized for this purpose. In yet another version, a single strand may be chemically synthesized one nucleotide at a time, such as in an oligonucleotide synthesis process. A single strand can also be obtained by purification from a natural source, such as RNA from cells. If the strand is synthesized, the labels may be attached to the nucleotides before synthesis. The labels may be selected from types that do not obstruct any step of the synthesis, such as the polymerase reactions.

If both strands are labeled and imaged, each base pair can be identified twice using different labels. This redundancy can provide protection against failure to label a nucleotide as well as misidentifying the labels. But it may not be necessary to label every nucleotide type (i.e., adenine, cytosine, guanine, and thymine or uracil). For example, in one version three of four nucleotide types may be labeled while the fourth type remains unlabeled. During analysis of the electron microscope images, the three labeled nucleotide types may be located and the fourth unlabeled nucleotide type may be identified by, for example, the absence of a label at locations where a nucleotide is expected based on the locations of the labeled nucleotides.

Multiple strands of the same polymer may be labeled, a unique label being applied to each of the different strands of the polymer. Each label may identify a corresponding structural unit. Each of these strands may be imaged and evaluated separately. After the positions and identities of the labels on each strand are evaluated, the label type and position information from the multiple strands may be combined to generate a sequence that contains all of the labeled structural units. For example, in the case of a nucleic acid, one strand may be labeled at its adenine (A) and cytosine (C) nucleotides, while the other strand is labeled at its guanine (G) and thymine (T) or uracil (U) nucleotides. The two strands may be imaged and evaluated separately. After the positions and identities of the labels on each strand are evaluated, the information from the two strands may be combined into a full sequence.

FIG. 1 is a schematic diagram of an exemplary embodiment of a STEM 10 that may be used for polymer sequencing. A specimen 20, which can be placed in STEM 10 for imaging, may include a sample (not shown) containing a polymer to be imaged and a substrate (not shown) to support the sample across an area that can be exposed to an electron beam probe. The sample may include one or more polymer strands, such as strands of DNA or RNA. However, the sample may be of any quantity, may be of any shape or size, and may include any desired features. For example, the sample may include a specific configuration for a desired application or parameter setting. In another embodiment, the sample is a test sample used for testing or optimization purposes, such as gold nanoparticles. The substrate may include a layer of crystalline or amorphous carbon. Alternatively or in addition, the substrate may include boron nitride, silicon, silicon dioxide, aluminum, polymeric resins, or organic materials. Specimen 20 may be supported by a stage (not shown).

STEM 10 includes an electron beam source 30 to generate an electron beam 40. Electron beam source 30 may be adapted to generate an electron beam having a current of less than about 100 mA. For example, for many applications electron beam source 30 may generate a beam current of from about 10 picoamps to about 1 milliamp. In an especially low-current version, however, electron beam source 30 may be adapted to generate electron beam 40 to have a current of less than about 10 µA, such as less than about 10 pA.

Electron beam 40 travels from source 30 through an optical system. The optical system may define an optic axis 50 along which electron beam 40 travels. The optical system may include illumination optics 60. Illumination optics 60 may include condenser lenses 70A-C to form electron beam 40 into a collimated probe 80 that illuminates specimen 20. Condenser lenses 70A-C may consist of, for example, two, three (as shown in the figure), or four lenses. Condenser lenses 70A-C may be magnetic or electrostatic. Illumination optics 60 may also include an aberration corrector 90 to correct for aberrations of electron beam 40 caused by the optical system.

The optical system of STEM 10 may also include an objective lens 100 to focus electron beam 40. An objective aperture 110 may be provided in the back focal plane of objective lens 100 or a plane conjugate to the back focal plane to define an acceptance angle, referring to an angle of electron beam 40 that is transmitted through aperture 110 and allowed to illuminate specimen 20. The rays that objective lens 100 focuses to probe 80 on specimen 20 are thus limited in angle by aperture 110.

Larger acceptance angle may improve resolution. Because of this relationship between the acceptance angle and resolution of STEM 10, the acceptance angle can be selected based on the desired resolution. For example, if 1 Ångström resolution at 100 kilovolts is desired, it may be desirable to have at least about 30 milliradians acceptance half-angle, or even at least about 40 milliradians acceptance half-angle. In one example, single-atom resolution—namely resolution at least as good as about 0.3 nanometers and in some instances at least as good as about 0.15 nanometers—may be desirable for a DNA-sequencing application. However, with an angular range that is unnecessarily high, current may be wasted undesirably. Once a suitable accelerating voltage is chosen, the desired resolution may determine the acceptance angle of objective lens 100.

Electron beam probe 80 may be conical or elongated along an axis. In one version, one or more of electron beam source 30 and condenser lenses 70A-C are adapted to produce a longitudinally stretched electron beam probe. For example, electron beam 40 may have a current distribution that is approximately Gaussian along the longitudinal axis. In one version, the cross-section of electron beam 40 may be substantially elliptical.

FIG. 2 illustrates an example of an embodiment of an electron beam 40 that is shaped into a longitudinally stretched probe 80A. In this example, the condenser lenses are multipoles 120A, 120B are combined to condense a round beam into longitudinally stretched probe 80A. Electron beam 40 is converged from a first cross-section 130A into a second cross-section 130B that is substantially oblong and then, at specimen 20, into longitudinally stretched probe 80A. At specimen 20, longitudinally stretched probe 80A is scanned along length of a sample 140. FIG. 3A is a plot of an example of the current distribution of the electron beam across the 'A' axis at the sample in FIG. 2, while FIG. 3B is a plot of an example of the current distribution of the electron beam across the 'B' axis.

Figure 4A:
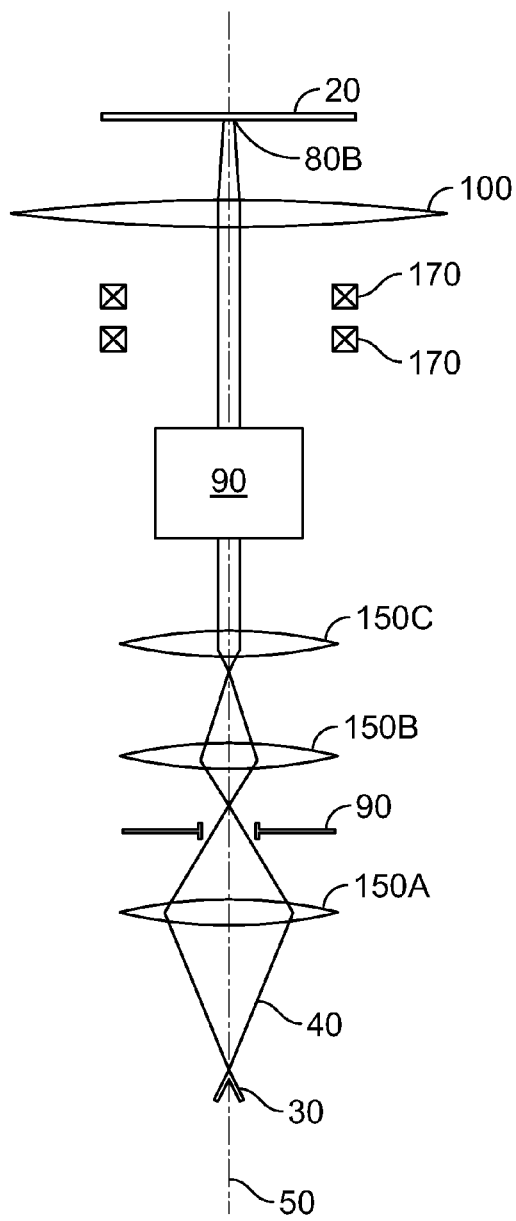
FIG. 4A is a schematic side view of an example of an embodiment of lenses that shape an electron beam into a longitudinally stretched probe with enhanced current.
Figure 4B:
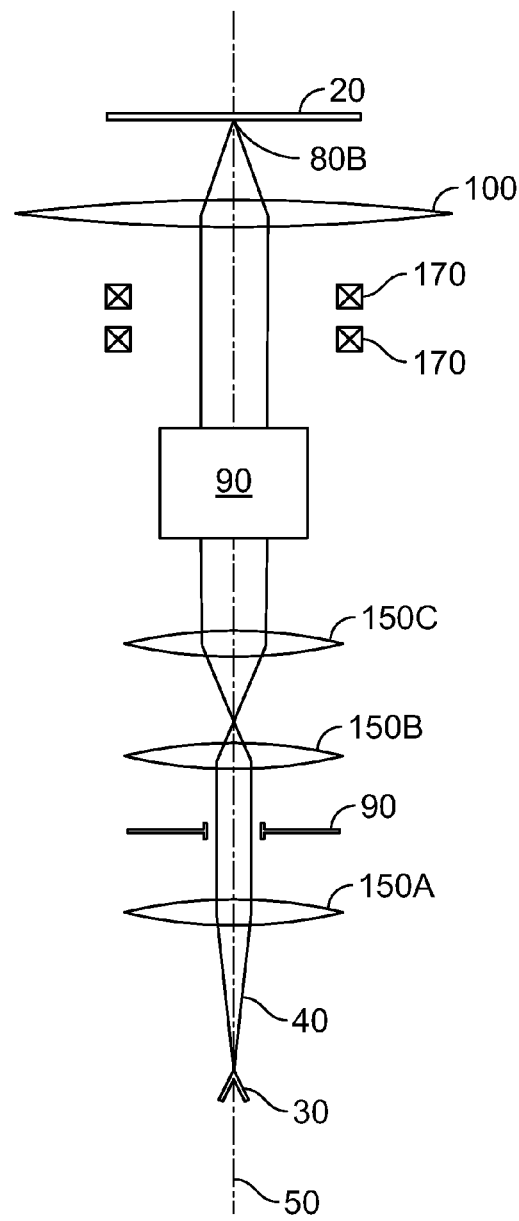
FIG. 4B is another schematic side view of the embodiment illustrated in FIG. 4A, from a perspective orthogonal to the perspective of FIG. 4A.

FIGS. 4A and 4B illustrate another example of an electron beam 40 that is shaped into a longitudinally stretched probe 80B. These figures show ray diagrams for electron beam 40 from two orthogonal side views, respectively, in an optical system. The components shown are similar to the optical components in FIG. 1, except that round condenser lenses 70A-C are replaced with optical elements 150A-C, which may each contain a combination of round lenses and multipoles. The flexibility of an illumination system created by breaking cylindrical symmetry allows different source demagnifications in multiple axes.

From the perspective of FIG. 4A along an 'A' axis, optical element 150A is run with a stronger excitation to collect a relatively large range of angles of electrons emitted from source 30 in objective aperture 90. Optical elements 150B-C form a relatively small beam that is subsequently sent into objective lens 100, forming a more parallel probe 80B. Because of the larger range of angles collected from source 30, the electrons that fill probe 80B are less coherent.

FIG. 4B illustrates a side view of the embodiment illustrated in FIG. 4A from a perspective along a 'B' axis that is orthogonal to the 'A' axis. From this perspective, probe 80B is similar to that created in FIG. 1 using condenser lenses 70A-C to collect a small range of angles of coherent electrons emitted from source 30 in objective aperture 90, and send them into objective lens 100 as a wide beam. Objective lens 100 forms these rays into a high-resolution probe 80B in the 'B' axis, by the inclusion of high-angle rays in the objective lens. The reduced coherence and reduced ray angles included in the probe 80B causes it to be larger in dimension along the 'A' axis than along the 'B' axis. This is demonstrated by the ray paths shown for electron beam 40 in FIGS. 4A and 4B. Beam scanners 170, discussed in more detail below, are also shown in the figure.

The large amount of source demagnification along the 'B' axis, when coupled with the small amount of source demagnification along the 'A' axis, creates a filled electron beam with enhanced current that is formed into shaped probe 80B. In this case, relaxation of the resolution along one axis provides for increased current along that axis.

One or more beam scanners 170 may be provided to scan electron beam 40 across specimen 20. Beam scanners 170 may scan electron beam 40 by generating either a magnetic or an electric field. For example, beam scanners 170 may include scan coils that generate an alternating magnetic field. Beam scanners 170 can be excited with ramp waveforms, causing the collimated probe to be scanned across the sample and thereby producing an intensity signal at the detector unique to the location of the probe on the sample. FIG. 1 shows an example of electron beam 40 being scanned between a first position 180A and a second position 180B.

Figure 5:
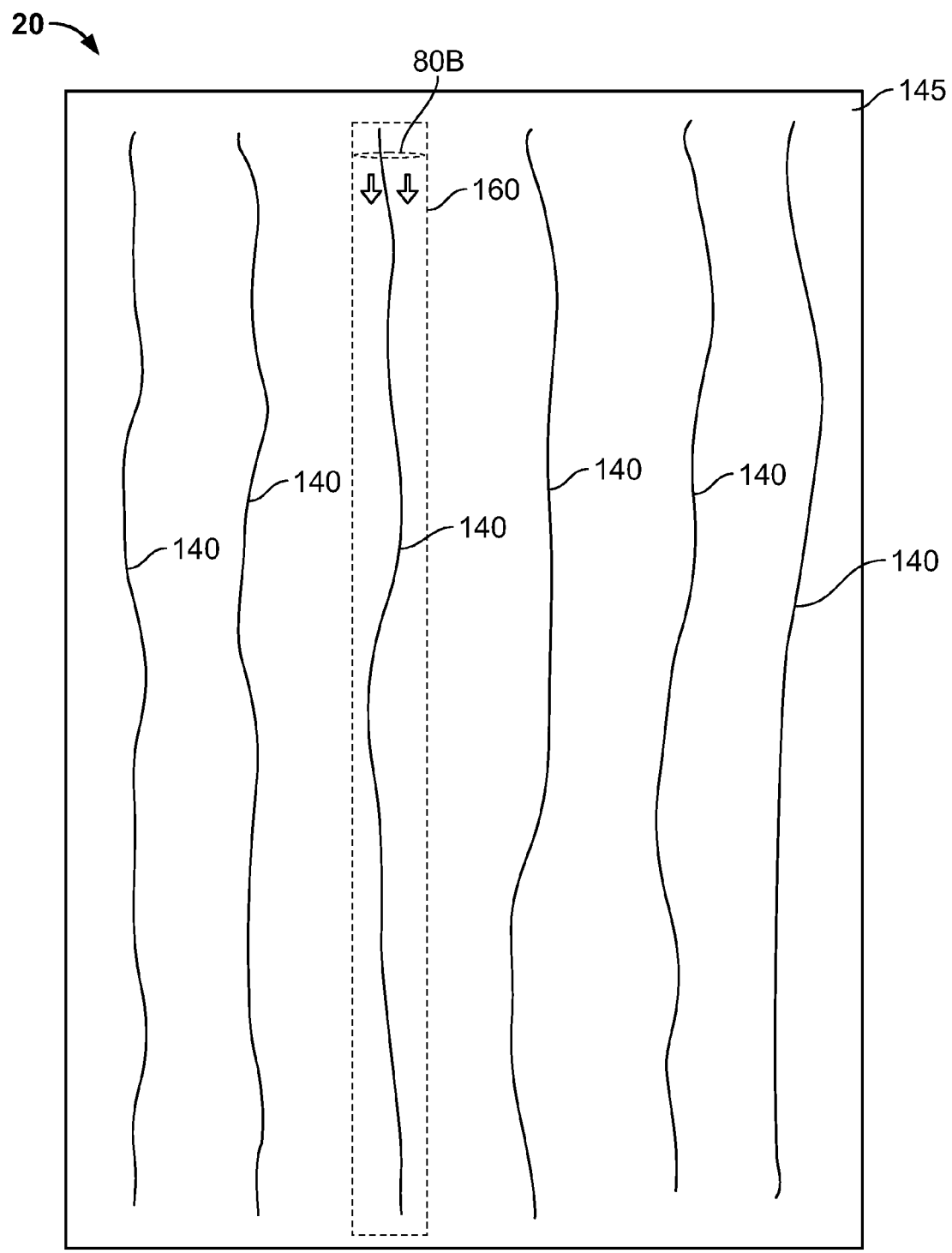
FIG. 5 is a schematic top view of an example of an embodiment of a sample that includes polymer strands on a substrate and a longitudinally stretched electron beam probe being scanned along the length of one of the polymer strands.

Longitudinally stretched electron beam probe 80B can be used to scan polymer strands of sample 140. For example, polymer strands may be scanned, one after the other, by longitudinally stretched probe 80B. FIG. 5 illustrates a schematic top view of an example of an embodiment of sample 140 that includes polymer strands on a substrate, and a longitudinally stretched electron beam probe scanning an area 160 that covers the length of one of the polymer strands. While probe 80B may be scanned along one axis, it may not be necessary, due to the shape of probe 80B, to scan the probe along an orthogonal axis in order to track each of the polymer strands. At each of the polymer strands, the extended length of stretched probe 80B may ensure that, all the way along the polymer strand, electron beam probe 80B illuminates the polymer strand somewhere along its length. The polymer strand may be sufficiently straightened on substrate 145 that its side-to-side movement along its length is smaller than the length of longitudinally stretched probe 80B. Sample 140 thus causes scattering of the electron beam and its effect is present in the image. Accordingly, since scanning transverse to the strand can be eliminated, the longitudinally stretched shape can reduce the number of pixels needed for suitable imaging.

Returning to FIG. 1, the electron beam energy used in STEM 10 may be determined at least in part based on the transmission properties of specimen 20. The substrate may have a thickness on the order of 2 nanometers, such as for example a thickness of about 1 nanometer. In one example, the substrate is made of carbon, although single-atomic-layer graphene may also be used. As a result, 1 keV electrons are likely to be the lowest energy appropriate when considering voltage alone.

When specimen 20 is illuminated, electrons scatter from specimen 20, emerging from the other side in a pattern that is collected by one or more detectors 190A, 190B (scattered rays not shown), 190C, 190D. Atoms of the sample having higher atomic number scatter the electrons to higher angles, while lighter atoms scatter the electrons to lower angles.

STEM 10 may have descanning and projection optics 200. The descanning optics may de-scan scattered electron beams 210A, 210B, thus, for example, realigning beam 210B with optic axis 50. The descanning optics may comprise, for example, descanning coils that may be symmetric to scan coils of beam scanners 170. The projection optics may include magnifying lenses that allow additional manipulation of scattered electron beams 210A, 210B.

Detectors 190A-C are provided to detect electrons, such as electron beams 210A, 210B, emerging from specimen 20 at one or more angles, respectively. Detectors 190A-C may be located on the side of specimen 20 opposite from electron beam source 30. For example, detector 190A may be provided to operate in a HAADF mode in which high-angle electron beam 210A is detected, detector 190B may operate in a MADF mode, and detector 190C may operate in a bright-field mode in which axial electron beam 210B including a zero beam is detected. Detectors 190A-C may comprise, for example, a scintillator and a charge coupled device (CCD). The scintillator may include one or more concentric annular detector rings and a central circular disc detector in an approximately cylindrically symmetric detector arrangement to receive the electrons. There may be apertures between detectors 190A-C. For each range of angles, detectors 190A-C may provide an intensity signal corresponding to current received for that angular range.

Alternate signals such as secondary electrons, backscattered electrons, and x-rays produced by the interaction between electron probe 80 and the sample may also be simultaneously detected in the region near the sample by one or more detectors 190E.

The geometry of STEM 10 may be able to more efficiently collect coherent electrons from source 30 compared to conventional TEM. Moreover, the geometry of source 30 and detectors 190A, 190B may provide a relatively high signal-to-noise ratio. The geometry of detector 190A distinguishes low-angle scattering from high-angle scattering to make contrast in the image depend on atomic number (Z). This efficiently acquires signal from labels that include heavy elements. This image data can be directly interpreted, unlike typical image data from conventional, phase-contrast TEM images, and may also have a higher signal-to-noise ratio. The use of the focused probe and annular detector geometry by STEM 10 also intrinsically acts as a filter to increase image contrast between heavy and light elements of specimen 20. Thus, STEM 10 may be adapted to have a higher resolution than conventional, phase-contrast TEM (for example, about 1 Ångström), making it especially advantageous for single-atom labels.

STEM 10 may be adapted to operate in a "bright field" mode in which a detector, such as detector 190C, detects a "forward-scattered" or "central" beam 210B of electrons emerging from specimen 20. Forward-scattered beam 210B refers to the zero beam (i.e., the 0 scattering vector, referring to the beam whose direction is identical to the orientation of beam 40 impinging on specimen 20) and a small range of angles around the zero beam. The bright-field mode may be particularly sensitive to the energy loss of the electrons, indicating chemical composition. These electrons can be detected to determine, for example, bonding energies of molecules that compose the sample.

In one version, a detector 190D may be provided to detect electrons in one or more preselected range of energies. Coupling optics 220 may be provided and detector 190D may include an electron prism 230 to filter out electrons that are not in the preselected energy ranges. In one version, this is used for electron energy loss spectroscopy (EELS). Electron prism 230 may, for example, generate an electric or magnetic field by using electrostatic or magnetic means, respectively. The field strength and dimensions of electron prism 230 may be selected such that, when the electrons of varying energies pass through the field, the electrons in the preselected energy range are transmitted through electron prism 230 while the remaining electrons are blocked. Detector 190D may also include a receiver 240, such as including a scintillator and CCD, to receive the transmitted electrons and convert that current into a detection signal. The EELS detection signal can be expressed as a plot 250 of current as a function of electron energy loss.

Alternatively to the bright-field mode, the STEM may be adapted to operate in a dark-field mode in which one or more electron beams 210A emerging from specimen 20 within a particular angular range are detected. Since specimen 20 is illuminated at approximately a point, this angular range of detection can be tightly controlled. For example, the dark-field mode may be an annular-dark-field (ADF) mode in which an electron beam shaped as a hollow cone of preselected thickness is detected. The dark-field mode may involve detecting a hollow cone at higher angles, which is referred to as high-angle annular-dark-field (HAADF) mode. The dark-field mode may also be a medium-angle dark-field (MADF) mode, in which a range of angles between the bright-field mode and the HAADF mode are detected. These dark-field modes can produce an image with monotonic contrast change with increasing atomic number, which enables direct interpretability of the image to determine relative atomic weights. For example, dark-field imaging can be used to obtain chemically sensitive projections of single atoms, clusters of atoms, or nanostructures. STEM 10 can also operate in simultaneous bright-field and dark-field modes. An electron beam source having a high-brightness gun may allow this mode to operate faster.

Each of detectors 190A, 190B in a cylindrically symmetric arrangement may limit the scattered electrons to an angular range denoted here as $\phi_d$, which defines an annulus between an inner angle $\phi_1$ and outer angle $\phi_2$. For an ADF mode these angles may be, for example, from about 25 mrad to about 60 mrad for $\phi_1$, and from about 60 mrad to about 80 mrad for $\phi_2$. For HAADF mode using detector 190A, these angles may be, for example, from about 60 mrad to about 80 mrad for $\phi_1$, and greater than about 100 mrad for $\phi_2$.

Alternatively to a cylindrically symmetric system, one or more of detectors 190A, 190B may have a shape that is cylindrically asymmetric. For example, detectors 190A, 190B may have an inner or outer perimeter that is polygonal, such as square or hexagonal. Alternatively, these detectors may have another shape that is cylindrically asymmetric.

In one version, the stage is moved continuously while electron beam 40 is simultaneously scanned. This may improve throughput by allowing continuous acquisition of images while eliminating the settling time caused by stop-start motion of a stage that is moved discretely and that may prevent acquisition of a still image of the sample. For example, a piezoelectric stage may be used. The piezoelectric stage may be able to move very quickly and smoothly so that short exposures on the order of milliseconds or microseconds can be practically achieved. The piezoelectric stage may also be adapted to move the stage with very high positional precision. Furthermore, the throughput of data that emerges from the detectors may be substantial, such that electronics capable of dealing with this data throughput downstream of the detectors may be desirable. In one embodiment, the stage motor is capable of displacing the specimen at a speed of at least about 100 nm per second.

In order to improve speed, accuracy, and sensitivity, aberration corrector 90 may correct for aberrations in electron beam 40, such as spherical aberrations and parasitic aberrations. The parasitic aberrations may or may not be cylindrically symmetric. Aberration corrector 90 may include electromagnetic lenses to correct for these aberrations. Parasitic aberrations may be caused, for example, by the optical elements having been machined in such a way as to be very slightly off-axis or very slightly non-round. Examples of commercially available aberration correctors for a STEM include Nion Co. quadrupole-octupole correctors (available from Nion Company of Kirkland, Wash.) and CEOS sextupole or quadrupole-octupole correctors (available from Corrected Electron Optical Systems GmbH of Heidelberg, Germany). In one example, aberration correction may improve resolution from about 2 to 3 Ångströms to about 1 Ångström. Labels that include clusters of atoms may be suitably imaged at 2 to 3 Ångströms. For labels that consist of single atoms, 1 Ångström resolution may be preferable.

STEM 10 may include a controller (not shown) to control operation of STEM 10. The controller may, for example, receive inputs from a human user, provide instructions to STEM 10, and/or perform data processing of images generated by STEM 10. The controller may automatically control one or more aspects of operation of STEM 10, and may even be adapted to entirely automate the operation of STEM 10.

The controller may control the components of the optical system, such as beam scanners 170 and the stage. Alternatively or in addition, the controller may receive one or more images from detectors 190A-D to be processed computationally. For example, the controller may process collected particle data and/or process any desired images. The controller may include an image formation unit for this purpose. The image formation unit may be disposed within or external to the STEM column and communicate with the optical system and the stage in any fashion, such as by a direct or indirect electronic coupling, or via a network.

The controller may include one or more microprocessors, controllers, processing systems, and/or circuitry, such as any combination of hardware and/or software modules. For example, the controller may be implemented in any quantity of personal computers, such as IBM-compatible, Apple, Macintosh, Android, or other computer platforms. The controller may also include any commercially available operating system software, such as Windows, OS/2, Unix, or Linux, or any commercially available and/or custom software such as communications software or microscope monitoring software. Furthermore, the controller may include one or more types of input devices, such as for example a touchpad, keyboard, mouse, microphone, or voice recognition.

The controller software, such as a monitoring module, may be stored on a computer-readable medium, such as a magnetic, optical, magneto-optic, or flash medium, floppy diskettes, CD-ROM, DVD, or other memory devices, for use on stand-alone systems or systems connected by a network or other communications medium, and/or may be downloaded, such as in the form of carrier waves, or packets, to systems via a network or other communications medium.

The controller can be adapted to automatically diagnose the magnitudes of various aberrations and apply compensating signals to the optical system, such as to aberration-producing lens elements and aberration corrector 90. One exemplary method is to raster scan one or more tuning regions of specimen 20 to generate an image and to analyze the generated image to extract information about aberrations that can be used to correct the aberrations. The tuning regions may be of any shape or size and may be located within or without the areas to be scanned. Another exemplary method is to acquire one or more images as a function of illumination tilt and defocus, and to extract the blurring effect of the tilt and defocus. The blurring gives a value for the defocus and astigmatism at a variety of angles. This process can provide sufficient data to numerically compute an aberration function for the imaging system. Yet another method is to defocus electron beam 40 and use bright-field detector 190C, such as a CCD camera, to generate a Ronchigram image, or a plurality of Ronchigram images taken at different positions of specimen 20, and then refocus electron beam 40 for continued imaging of the sample. The Ronchigram image can provide sufficient aberration information to derive optical parameters that permit suitable compensation for these aberrations.

A sample used for the purposes of diagnosing aberrations may contain single atoms or clusters of atoms, or may be another kind of sample made for the purpose of diagnosing aberrations. For example, the sample may be specimen 20 that is also the subject of interest for study. Alternatively, the sample may be a sample used solely for calibration of STEM 10.

STEM 10 may include or be connected to a power supply that provides power to components of STEM 10, such as electron beam source 30, condenser lenses 70A-C, objective lens 100, detectors 190A, 190B, the stage, and the controller.

In one embodiment, the optical system of STEM 10 has a total power consumption of less than about 2.5 kW.

The speed and quality of STEM imaging can be improved to make it advantageous for polymer sequencing. First, STEM 10 may use a longitudinally stretched probe, such as described above. Second, STEM 10 may selectively direct the imaging along the sample. In this way, speed can be improved by from about 10 to about 100,000 times when compared to conventional TEM or STEM imaging. Third, STEM 10 may automatically tune the optical system one or more times during imaging, such as to refocus and compensate for aberrations.

STEM 10 may have a characteristic area at the plane of specimen 20 in which optical characteristics, such as, for example, resolution, are selected to be within a range suited to the imaging that is performed. This area may be referred to as the "field of view" of STEM 10. In one embodiment, for example, the field of view is substantially free of "coma," a second-order type of parasitic aberration, and/or astigmatism. In one example provided solely for the purpose of illustration, the field of view has a diameter of about 1 to about 2 microns. Within the field of view, electron beam 40 may be scanned in one or more scanning areas across specimen 20 by electronic shifting, such as by generating an electric or magnetic field, while remaining within the desired range of optical characteristics (such as high resolution).

Figure 6:
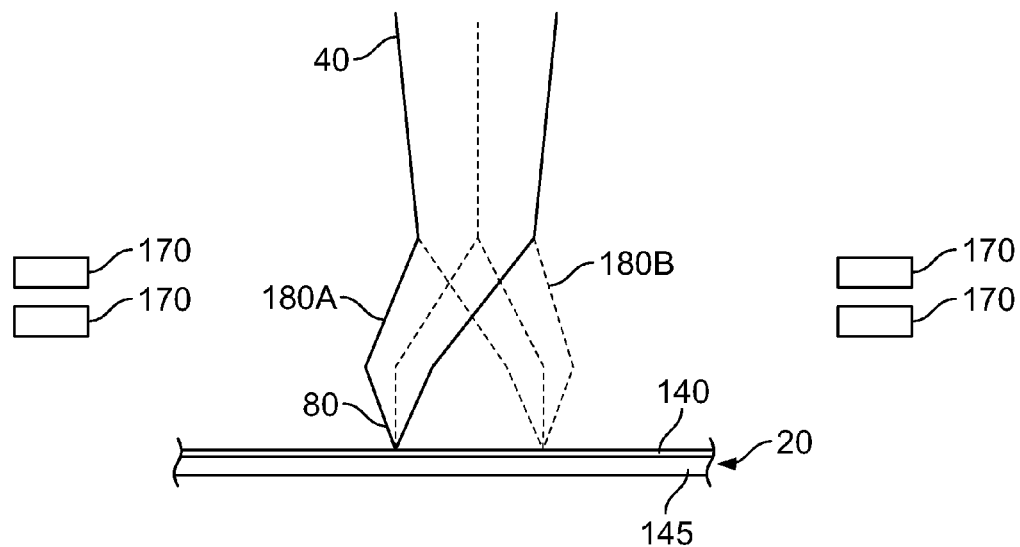
FIG. 6 is a side view of a schematic diagram of a portion of an example of an embodiment of a STEM in which a beam scanner electronically shifts an electron beam from a first position to a second position.
Figure 7:
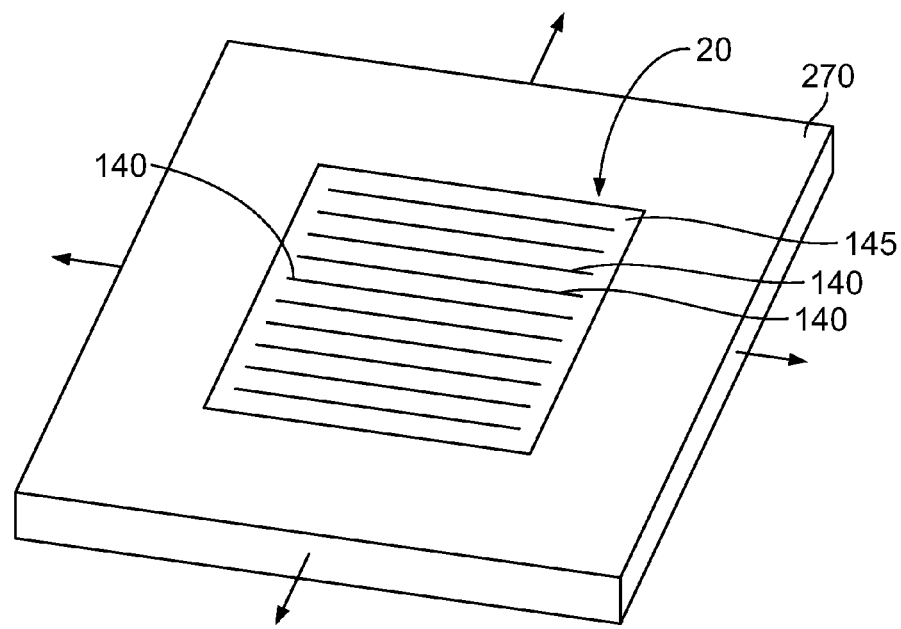
FIG. 7 is a three-dimensional schematic perspective view of an example of an embodiment of a stage supporting a specimen that can be moved back and forth along at least two orthogonal axes in relation to the microscope.

FIG. 6 illustrates an example of an embodiment in which electron beam 40 is electronically shifted from a first position 180A to a second position 180B on specimen 20, such as to scan electron beam 40 from a first location to a second location to move electron beam 40 between two different samples. As shown in the figure, beam scanners 170 may generate a magnetic or electric field that deflects electron beam 40. If an area of specimen 20 that is currently outside the field of view is to be scanned, that area can be brought into the field of view, such as by moving the stage carrying specimen 20. FIG. 7 illustrates an example of an embodiment of a stage 270 supporting specimen 20. In this example, stage 270 can be moved back and forth along two orthogonal axes in relation to the rest of the microscope by one or more stage motors (not shown). To scan one or more regions that fall outside the dimensions of a single field of view, stage 270 may be moved either between imaging cycles or simultaneous with continuous imaging. Stage 270 may also be moved along a third axis that is orthogonal to the other two axes, such as a "height" axis substantially parallel to the optic axis. Defocus may be accomplished by adjusting the stage position on this third axis, which may be done rather than adjusting optical parameters, for example signals applied to the condenser and objective lenses. Furthermore, the beam scanners and stage motors may be used together, such as where the stage motors are used to move the stage continuously during imaging along one axis while the beam scanners raster scan electron beam 40 along an approximately orthogonal axis.

Within each field of view, the STEM may define one or more scanning areas in which the electron beam will be scanned to contribute to the final image. The STEM may perform the imaging of sample 140 in one or more cycles corresponding to the scanning areas, each imaging cycle for a scanning area yielding a contribution that is referred to here as a sub-image. Each scanning area may be noncontiguous, contiguous, or overlapping in relation to scanning areas within the same field of view or scanning areas in different fields of view. Moreover, the scanning areas may even be a combination of noncontiguous (i.e., with edges separated by a space), contiguous (i.e., edge to edge), or overlapping.

In one example provided solely for the purpose of illustration, the microscope has a resolution of about 1 Ångström. For a DNA strand, in one embodiment in which a heavy label is attached to a single type of nucleotide, one may expect the presence of a heavy label at about every 15 to about every 25 Ångströms. Multiple scanning areas may be defined within the field of view, each scanning area having dimensions of from about 500 pixels by about 500 pixels to about 2000 pixels by about 2000 pixels. For example, each scanning area may have rectangular dimensions of about 500 pixels by about 2000 pixels. In another example, each scanning area is a strip with dimensions of about 5 pixels by about 8000 pixels.

Noncontiguity between certain scanning areas, such as resulting from defining the scanning areas to track different strands of sample 140, may yield an increase in speed by allowing the imaging process to avoid unnecessary scanning, such as unnecessary scanning of "empty" regions where portions of sample 140 are not actually present. For example, the controller may define scanning areas that track, in two dimensions in the plane of specimen 20, the location of a sample that consists of multiple DNA strands that have been straightened out across substrate 145. In one embodiment, noncontiguity of scanning areas may allow the STEM to operate at least 100 times faster than a conventional STEM.

Overlapping scanning areas, meanwhile, may provide imaging redundancy that can be used to ensure accuracy of the eventual sequencing results. In one embodiment, overlapping of scanning areas corresponding to different stage positions may be desirable. This may be advantageous, for example, if hysteresis in the movement of stage 270 is present such that stage positioning is inexact in relation to the resolution of imaging. In this case, redundancy in imaging may make up for the inexactitude of positioning. For scanning areas within the same field of view, between which the electron beam is electronically shifted, beam positioning may be sufficiently exact to use scanning areas that are contiguous or overlap by a smaller amount.

The STEM may perform a preliminary imaging of sample 140 before the main imaging of sample 140 that is used to obtain the sequence information. The preliminary imaging may be, for example, a faster, lower-resolution, or lower-dose scan of sample 140 used to determine the location of sample 140, such as the locations of each of multiple polymer strands that make up sample 140. This scan may, for example, cover a substantially contiguous area, rather than being limited to particular, discrete scanning areas. Surveying may also be performed outside of the STEM, where fiducials on specimen 20 or another registration mechanism is provided, such as using a scanning electron microscope (SEM) or alternatively an optical microscope (such as for fluorescent or light-visible markers). The controller may then define the scanning areas such that the scanning areas track sample 140 based on the determined location of sample 140. Using the scanning areas, the controller may perform a slower or higher-resolution scan within the scanning areas, thus concentrating the imaging on the actual location of sample 140 and thereby improving efficiency. For example, within each scanning area the microscope may raster scan the electron beam.

After the sub-images are obtained, the controller may stitch together the sub-images to produce a partially or wholly comprehensive image of sample 140. For example, where there are overlapping or contiguous sub-images, these sub-images may be joined together to yield imaging data that is continuous across the corresponding scanning areas. For overlapping sub-images, the controller may use the redundant image information at the overlap to accurately join the sub-images together into a comprehensive image. In this way, the sequence information from the polymer can be obtained without gaps or inaccurate repetitions.

Tracking the sample may become even more advantageous when the polymer strands of sample 140 are less straightened. A polymer strand with more curvature and that does not overlap with itself, for example, may occupy more area on the substrate in relation to its length. The STEM, by defining scanning areas that track the paths of the polymer strands, may be able to avoid even more empty area where the polymer strands are not present, providing faster imaging speeds.

The controller may evaluate information originating at one or more of the detectors, either between imaging cycles or simultaneous with imaging, to determine the current quality of imaging. In one version, imaging information from dedicated "tuning regions" is used. However, the images themselves may additionally or alternatively be used. For example, information from the most recent images can be used to determine trends of tuning deterioration. This evaluation can be used to set optical parameters of the STEM to improve the quality of imaging. For example, returning to FIG. 1, the optical parameters may be applied to condenser lenses 70A-C, objective lens 100, aberration corrector 90, and the stage. For example, the optical parameters applied to condenser lenses 70A-C, objective lens 100, and the stage may improve the focus, while the optical parameters used on aberration corrector 90 may compensate for higher orders of aberration. This process may be referred to as "re-tuning" the microscope.

It may be desirable to maintain the microscope in a substantially steady state in terms of contamination and stability during imaging. But the performance of the optical system may tend to deteriorate over time. In one example, the optical system may deteriorate to an undesirable state in from about 5 to about 30 minutes, such as about 15 minutes. When this happens, it may become advantageous to perform re-tuning. In one version, first-order and second-order aberrations may be especially prone to deterioration and/or advantageous to compensate for by re-tuning. The electron beam source may also deteriorate over time. To refresh the electron beam source, it can be "flashed" by running a high current through it between beam scanning cycles. This causes a localized heating of the filament that reconditions the source.

Re-tuning may be triggered according to any suitable procedure. The controller may monitor the microscope to initiate the determination of imaging quality, the controller may automatically initiate re-tuning at regular intervals, or the controller may poll a store of recently generated images to determine image quality as a background process. For example, the re-tuning may be triggered within any desired time interval, such as within any quantity of hours or minutes, or subsequent to any quantity of images generated by the microscope or every Nth linear scan or scan cycle performed by the microscope. In an exemplary embodiment, the controller initiates re-tuning between sequential fields of view. In another embodiment, however, the controller can re-tune the optical system between sequential scanning areas.

At each of the sub-areas, STEM 10 may scan and image a tuning region within or without the sub-area one or more times to generate one or more sub-images that can be used to track the sample and/or produce imaging metadata. The imaging metadata may include, for example, focus error and amounts of various orders of aberration, and beam current. The controller may use the imaging metadata to generate optical parameters to improve image quality, such as, for example, to autofocus the image at the elevation of sub-area. For example, the controller may evaluate several sub-images taken in a particular area to determine the magnitude and direction of focus error. Using this information, STEM 10 can generate a final well-focused sub-image that will be used for evaluation of the sample itself. STEM 10 may use any number of sub-images of a sample to determine imaging metadata. The sub-images may cover any desired variation range for a particular parameter.

In analyzing an image, the controller may analyze any suitable characteristics of the image, such as intensity, pixel counts, or power, each of which may be analyzed in real space or in frequency space (so that intensity may be within or without a spatial frequency range). When comparing images or evaluating a series of images, the controller utilizes any characteristic that differs between the images, such as in a preselected region of the images.

The controller may also use any number of images for the image quality comparison, where the image quality values for current and prior images may be combined in any suitable fashion, such as averaged, weighted, or summed. A user threshold for image quality may be set to any suitable value. A comparison of image quality values may utilize any mathematical or statistical operations to determine image quality compliance, such as a comparison, statistical variance, or deviation.

The STEM imaging process may be performed entirely automatically, such as after initiation by a user or initiation by a larger process of which the STEM imaging is a subprocess. Parameters may be determined automatically and applied to the microscope. Alternatively, any part of the technique, such as scanning of images, determination of parameters, or application of the parameters, may be performed manually. For example, the computer system may provide the optimal settings to a technician that manually applies the settings to the microscope. The microscope controller may perform any desired processing, such as monitoring and adjustment of optical parameters or image formation and processing. For example, the controller may align images using image registration algorithms. The controller may also adjust the aberrations and defocus of an image based on characteristics of a previous image.

In one exemplary embodiment, imaging of the scanning areas may proceed as follows. The controller may initiate imaging by STEM 10 by scanning a first scanning area in a first field of view. For example, the electron beam may be raster scanned throughout the first scanning area. Moreover, the scanning area may be scanned more than once, such as to try different optical parameters or otherwise improve imaging quality. When a useful sub-image for the first scanning area has been generated, the controller may control the microscope to begin scanning a second scanning area in the same field of view, if there is any. After all the scanning areas in the field of view have been imaged, the stage may be moved into a new field of view. The process described above may be repeated until all planned fields of view have been scanned.

Alternatively to sequentially scanning the scanning areas that are in the same field of view, moving from one scanning area to the next after scanning is complete for the previous scanning area, the controller may control STEM 10 to scan multiple scanning areas in parallel, such that more than one scanning area is scanned before any of them has been completely scanned. In one exemplary embodiment, STEM 10 may scan proximate regions of multiple scanning areas before completing the scanning of any of these scanning areas. This may be advantageous, for example, where the scanning areas are shaped as elongated strips lined up in parallel, each elongated strip corresponding to a polymer strand, such that the strips are of different length as constrained by the boundary of the field of view.

The set of sub-images that coincide with the length of the sample may be stitched together into a comprehensive image. Automatic re-tuning may be able to yield, without substantial user intervention, a high-quality comprehensive image suitable for extracting the sequence information of the polymer. The controller can then analyze the image to identify the structural units of the polymer being sequenced, such as by identifying the labels attached to the polymer.

Figure 8:
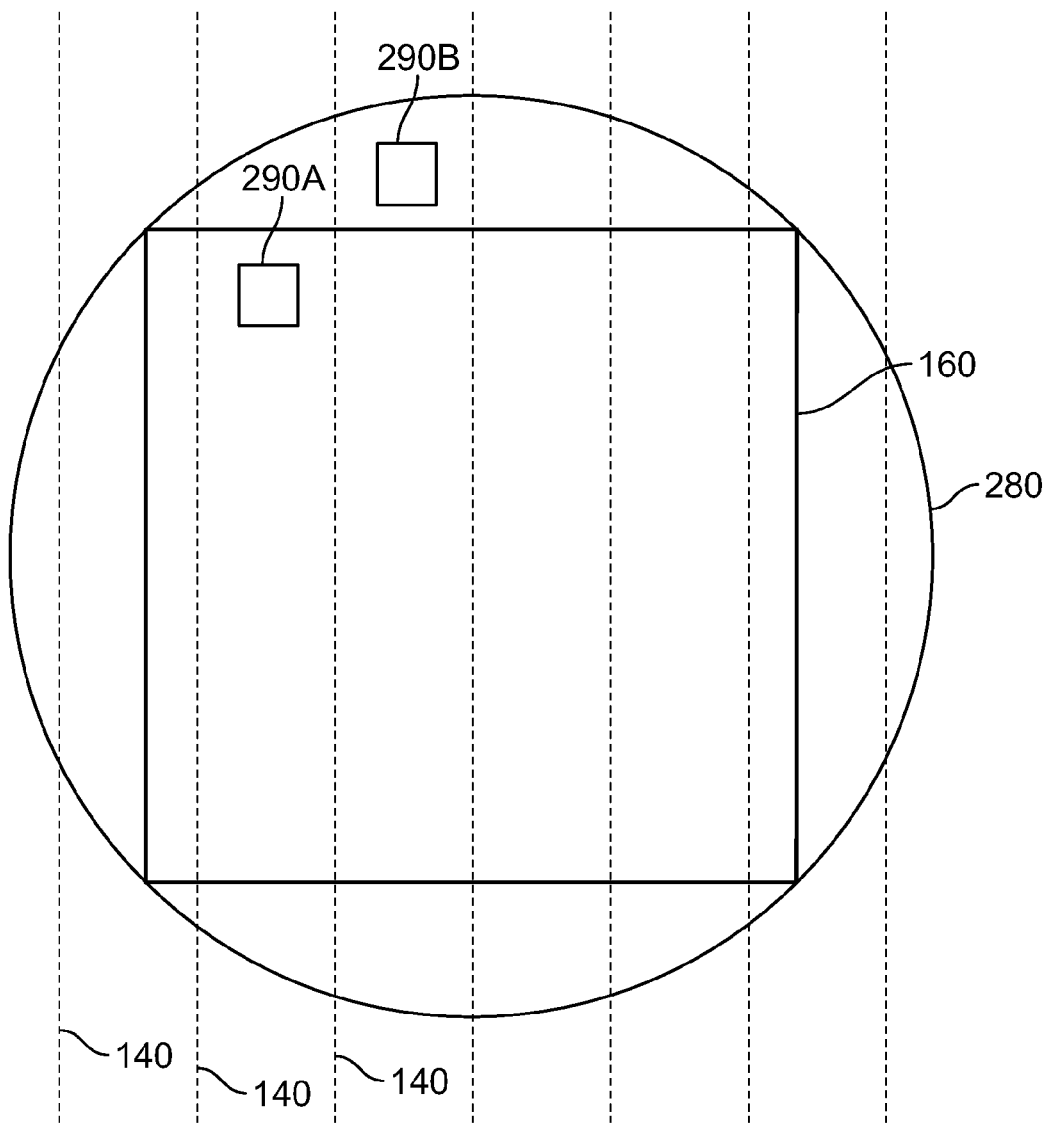
FIG. 8 is a schematic diagram of an example of an embodiment of a field of view that encloses a single defined scanning area covering a region of a sample that includes multiple polymer strands.

FIG. 8 illustrates an example of an embodiment of a field of view 280 enclosing a relatively large scanning area 160, such as nearly the size of field of view 280, that covers a region of sample 80 that includes multiple polymer strands. A tuning region 290A inside scanning area 160 may initially be scanned to obtain optical parameters useful for automatically re-tuning the optical system of the microscope. Alternatively, a tuning region 290B outside the scanning area 160 may be relied on. However, it may be desirable to locate tuning region 290A, 290B to avoid covering the polymer strands themselves, such that the strands are not damaged by electron beam illumination. In one embodiment, the large size of scanning area 160 shown in this figure may be used at reduced resolution for a low-dose, high-speed survey to locate strands of sample 80. However, scanning area 160 does not have to be nearly the full size of field of view 280. It may be advantageous for scanning area 160 not to be of maximal size, since tuning drift may otherwise vignette the corners of scanning area 160. For example, scanning area 160 may have a size that is about 10 to about 20 times smaller in diameter than field of view 280.

Figure 9:
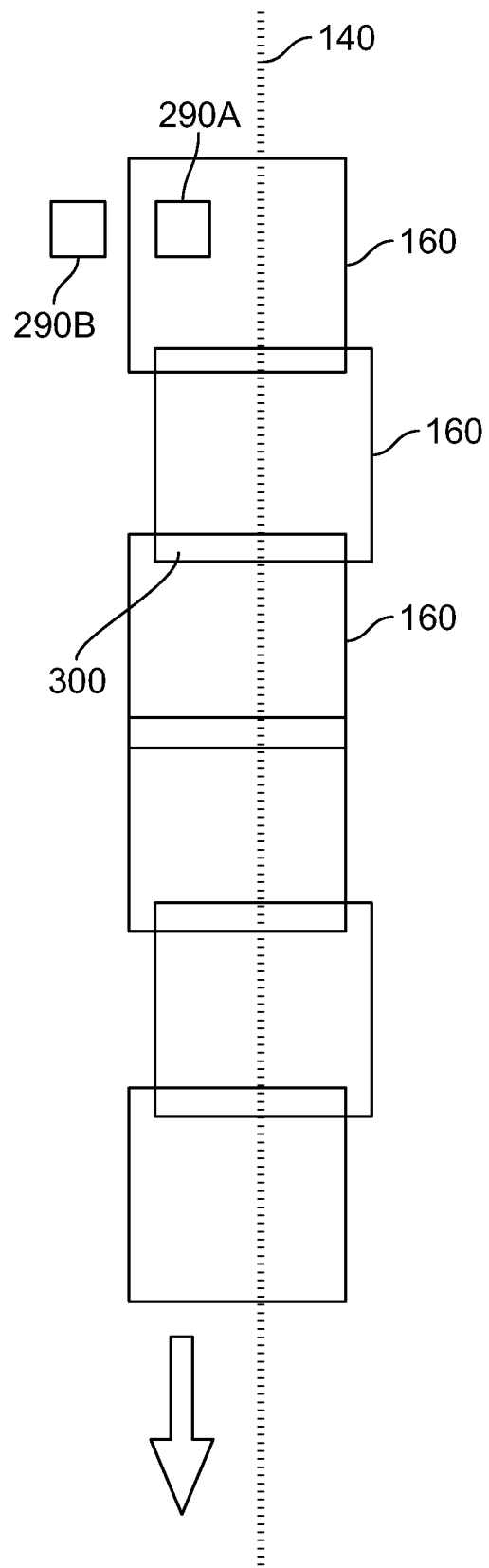
FIG. 9 is a schematic diagram of a wider perspective on scanning area of FIG. 8, showing a plurality of partially overlapping scanning areas.

FIG. 9 illustrates another perspective on scanning area 160 of FIG. 8, showing a plurality of scanning areas 160 that overlap at overlap areas 300. As shown in the figure, scanning areas 160 are arranged to track the sample, thereby improving imaging efficiency. Imaging information obtained redundantly from overlap areas 300 can be used to stitch together sub-images obtained from the different scanning areas 160, and to perform drift compensation and drift distortion correction. The electron beam may be moved between scanning areas 160 either by moving the stage or by electronically shifting the electron beam.

Figure 10:
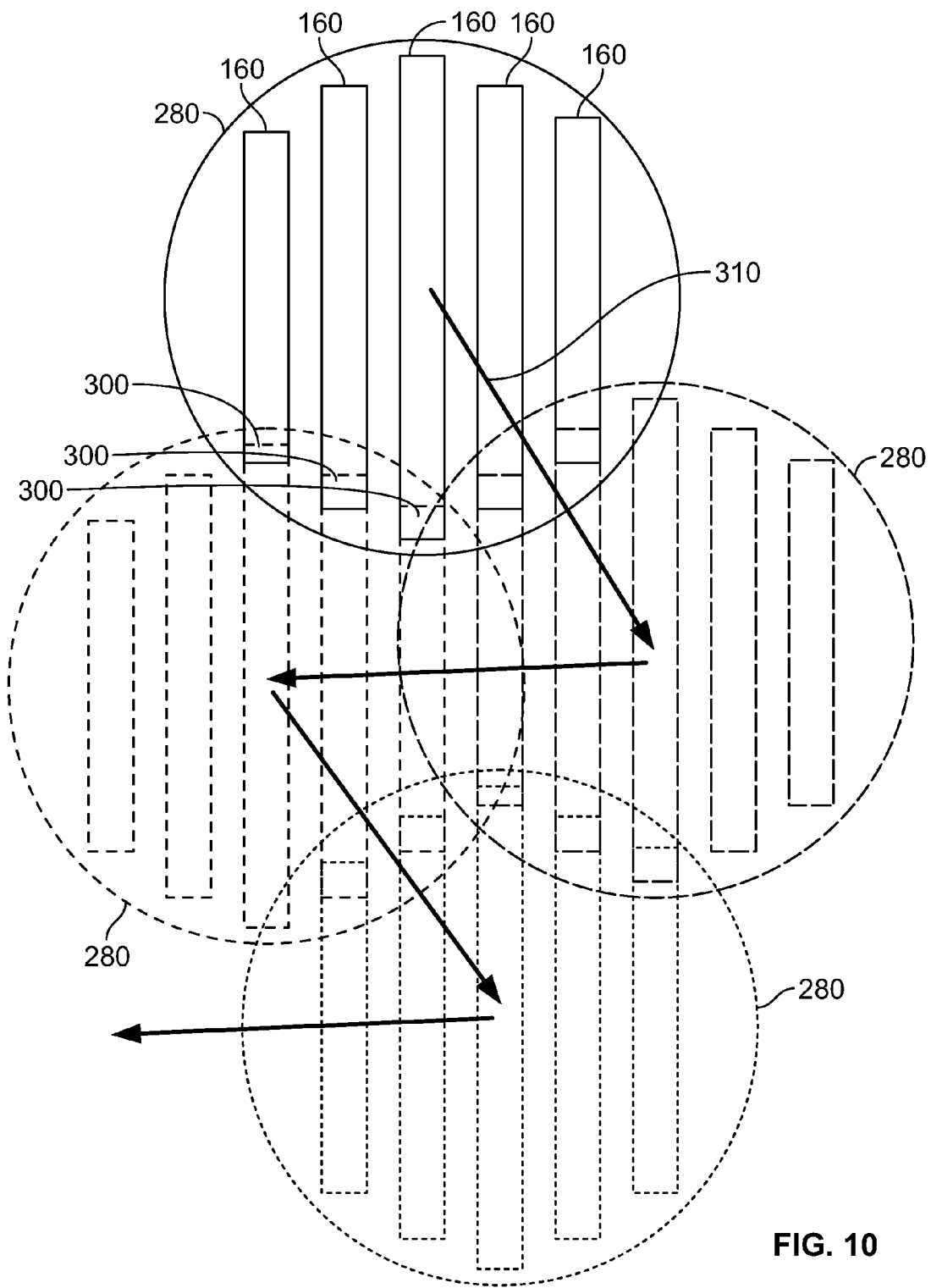
FIG. 10 is a schematic diagram of another example of an embodiment of a plurality of fields of view, wherein multiple scanning areas are defined within each individual field of view.

FIG. 10 illustrates another example of an embodiment of a plurality of fields of view 280. In this example, multiple scanning areas 160 are defined within each field of view 280. Scanning areas 160 may be shaped as elongated strips that overlie the polymer strands of the sample. Since scanning is confined to scanning areas 160, rather than having to scan the entire field of view 280, including the spaces between scanning areas 160, imaging speed is improved. Within each field of view 280, scanning areas 160 may be scanned sequentially in any order, or even in parallel (i.e., scanning parts of different scanning areas 160 before one of scanning areas has been completely scanned), as suited to the application. For example, the scanning order may be adapted to further improve the speed of imaging. The stage may be displaced to move along a path 310, from one field of view to the next, such as shown in the figure. Path 310 may be selected to provide suitably good coverage of the sample in a substantially efficient way. Within each of fields of view 280, the electron beam may be electronically shifted to scan across scanning areas 160.

Figure 11:
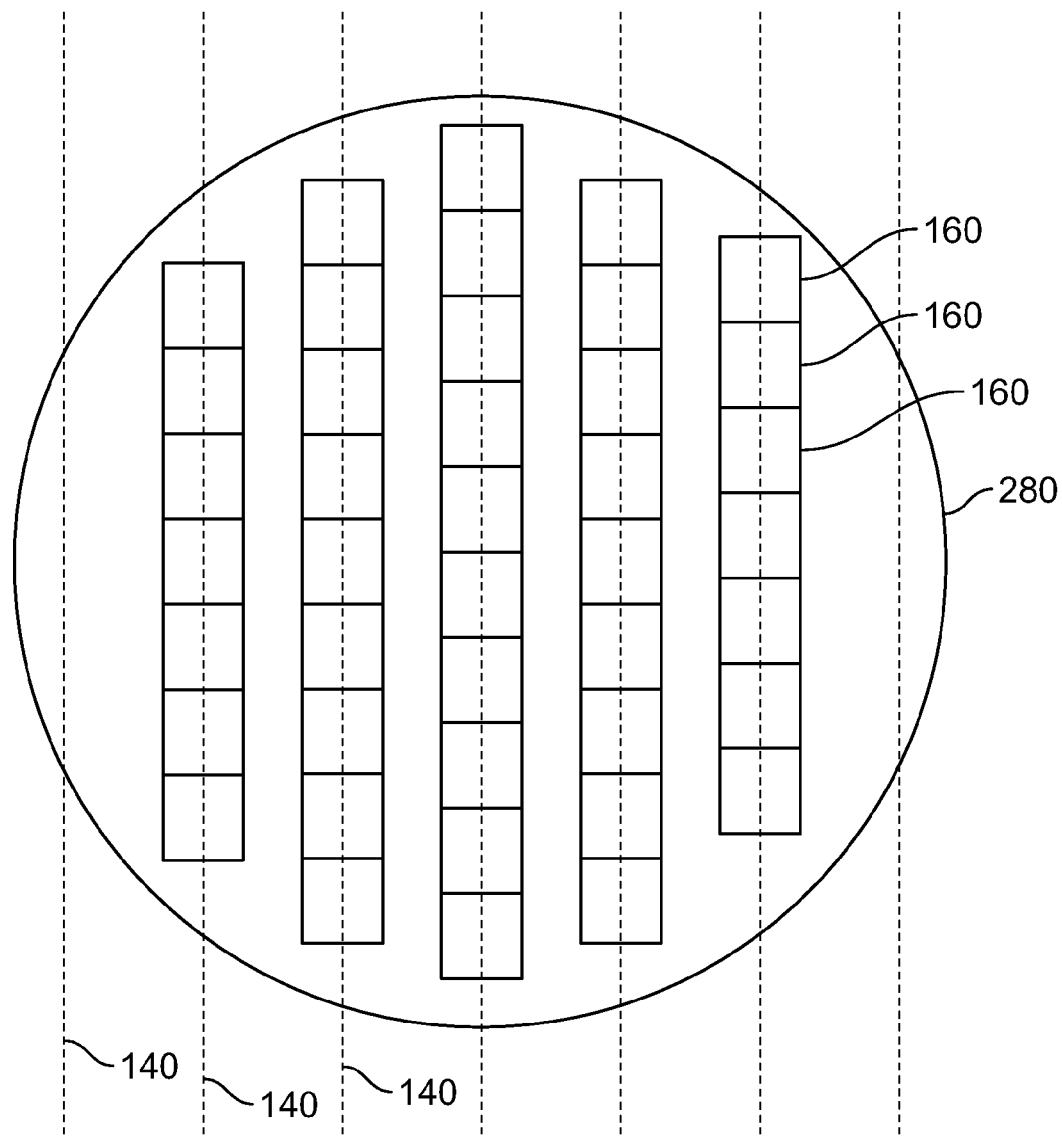
FIG. 11 is a schematic diagram of yet another example of an embodiment of a field of view, wherein the field of view encloses a plurality of scanning areas that are arranged as elongated strips overlying polymer strands of a sample.

FIG. 11 illustrates yet another example of an embodiment of a field of view 280 enclosing a plurality of scanning areas 160. In this example, scanning areas 160 are arranged in elongated strips that overlie the polymer strands of sample 140. However, unlike the example illustrated in FIG. 10, in this figure a plurality of contiguous scanning areas form each of the elongated strips. Between the elongated strips, scanning areas 160 are noncontiguous, separated by spaces that do not have to be scanned, thereby improving imaging speed. Within field of view 280, scanning areas 160 may be scanned sequentially in any order, or even in parallel, as suited to the application.

Figure 12:
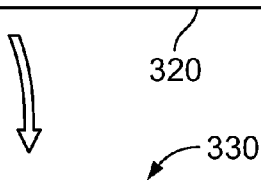
FIG. 12 illustrates an example of an embodiment of a mapping between the identified presence of each of multiple DNA labels and their corresponding nucleotide types, showing the sequence (SEQ ID NO:1) that results from the mapping.

FIG. 12 illustrates an example in which information 320 about the presence or absence of labels corresponding to particular structural units at particular positions along the lengths of a number of strands of a polymer are converted into the sequence of the polymer. In the case where the polymer is a nucleic acid, such as in the example illustrated, the labels correspond to particular nucleotide types (A, G, T, C). In the figure, each of the rows shows two portions of label information from imaged strands. The portions of label information may come from separate strands of the nucleic acid or different noncontiguous scanning areas. Using bioinformatics techniques, these portions of label information can be arranged as a function of corresponding position in the nucleic acid and then connected together. By combining this nucleotide information, sequence 330 of the nucleic acid can be determined. Where sub-images from two scanning areas have previously been graphically stitched together, as described above, there may not be any need to rely on bioinformatics techniques to connect the label information from the sub-images since the label information may already be continuous.

The STEM may be used in any suitable facility in any desired arrangement, such as networked, direct, or indirect communication arrangements. Moreover, the various functions of the STEM may be distributed in any manner among any quantity of components, such as one or more hardware and/or software modules or units. The hardware may include microscopes, machine managers, computer or processing systems, circuitry, networks, and image stores, that may be disposed locally or remotely of each other and may communicate with each other or be coupled to each other in any suitable manner, such as wired or wireless, over a network such as WAN, LAN, Intranet, Internet, hardwire, or modem, directly or indirectly, locally or remotely from each other, via any communications medium, and utilizing any suitable communication protocol or standard. The software and/or algorithms described above may be modified in any manner that accomplishes the functions described herein.

The embodiments of the STEM described herein may be implemented with either electrostatic or magnetic components. The STEM may include any quantity of electrostatic or magnetic components, such as an electron or other particle gun, lenses, a dispersion device, stigmator coils, electron detectors, and stages, arranged within or without the STEM in any suitable fashion. Image stores, files, and folders used by the STEM system may be of any quantity and may be implemented by any storage devices, such as memory, database, or data structures.

Implementation of aspects of the STEM, such as the image processing or aberration correction, may be distributed among the controller or other processing devices in any desired manner, where these devices may be local or remote in relation to one another. The controller may communicate with and/or control the microscope to perform any desired functions, such as scanning the specimen and generating the images or transferring images to memory.

Although the foregoing embodiments have been described in detail by way of illustration and example for purposes of clarity of understanding, it will be readily apparent to those of ordinary skill in the art in light of the description herein that certain changes and modifications may be made thereto without departing from the spirit or scope of the appended claims.

It is also to be understood that the terminology used herein is for the purpose of describing particular aspects only, and is not intended to be limiting, since the scope of the present invention will be limited only by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of ordinary skill in the art upon reading this disclosure, each of the individual aspects described and illustrated herein has discrete components and features which may be readily separated from or combined with the features of any of the other several aspects without departing from the scope or spirit of the disclosure. Any recited method can be carried out in the order of events recited or in any other order which is logically possible. Accordingly, the preceding merely provides illustrative examples. It will be appreciated that those of ordinary skill in the art will be able to devise various arrangements which, although not explicitly described or shown herein, embody the principles of the disclosure and are included within its spirit and scope.

Furthermore, all examples and conditional language recited herein are principally intended to aid the reader in understanding the principles of the invention and the concepts contributed by the inventors to furthering the art, and are to be construed without limitation to such specifically recited examples and conditions. Moreover, all statements herein reciting principles and aspects of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary configurations shown and described herein. Rather, the scope and spirit of present invention is embodied by the claims.

In this specification, various preferred embodiments have been described with reference to the accompanying drawings. It will be apparent, however, that various other modifications and changes may be made thereto and additional embodiments may be implemented without departing from the broader scope of the claims that follow. The specification and drawings are accordingly to be regarded in an illustrative rather than restrictive sense.

We claim:

1. A scanning transmission electron microscope for imaging a specimen, the microscope comprising:
an electron beam source to generate an electron beam;
beam optics to converge the electron beam;
a stage to hold a specimen in the path of the electron beam;
a beam scanner to scan the electron beam across the specimen;
a detector to detect electrons transmitted through the specimen to generate an image; and
a controller to (1) define one or more scanning areas corresponding to locations of the specimen, (2) control one or more of the beam scanner and stage to selectively scan the electron beam in the scanning areas, (3) generate a sub-image for each of the scanning areas, (4) stitch together the sub-images for the scanning areas to generate a stitched-together image, and (5) analyze the stitched-together image to determine information regarding the specimen.

2. The scanning transmission electron microscope of claim 1, wherein the controller is adapted to perform one or more of (i) drift compensation and (ii) drift distortion correction to generate the stitched-together image.

3. The scanning transmission electron microscope of claim 1, wherein the plurality of the scanning areas overlap, and wherein the controller is adapted to generate the sub-image for each of the scanning areas and stitch together the sub-images into a comprehensive image based on matching imaging information from the area of overlap.

4. The scanning transmission electron microscope of claim 1, wherein the plurality of the scanning areas are contiguous, and wherein the controller is adapted to generate the sub-image for each of the scanning areas and stitch together the sub-images into a comprehensive image based on matching imaging information from the areas near the contiguity.

5. The scanning transmission electron microscope of claim 1, wherein the specimen comprises an elongated object, and wherein the controller is adapted to control the microscope to selectively scan the electron beam substantially along the elongated object of the specimen.

6. The scanning transmission electron microscope of claim 1, comprising one or more detectors to detect electrons transmitted through the specimen to generate the image, and wherein the detectors and controller are adapted to tune the beam optics during imaging.

7. The scanning transmission electron microscope of claim 6, wherein the detectors and controller are adapted to tune the beam optics between cycles of scanning the electron beam.

8. The scanning transmission electron microscope of claim 6, wherein the detectors and controller are adapted to tune the beam optics between cycles of scanning areas corresponding to sub-images and generating the sub-images.

9. The scanning transmission electron microscope of claim 1, wherein the beam optics are adapted to converge the electron beam into a longitudinally stretched beam.

10. The scanning transmission electron microscope of claim 1, wherein the controller is adapted to define one or more of the scanning areas to be displaced in at least two dimensions in relation to each other, and wherein the controller is adapted to stitch together the sub-images by feature registration in at least two dimensions.

11. A method of imaging a specimen, the method comprising:
generating an electron beam;
converging the electron beam;
holding a specimen on a stage in the path of the electron beam;
defining one or more scanning areas corresponding to locations of the specimen;
controlling one or more of the beam scanner and the stage to selectively scan the electron beam in the scanning areas;
detecting electrons transmitted through the specimen to generate a sub-image for each of the scanning areas;
stitching together the sub-images for the scanning areas to generate a stitched-together image; and
analyzing the stitched-together image to determine information regarding the specimen.

12. The method of claim 11, comprising performing one or more of (i) drift compensation and (ii) drift distortion correction to generate the stitched-together image.

13. The method of claim 11, wherein the plurality of the scanning areas overlap, and comprising generating the sub-image for each of the scanning areas and stitching together the sub-images into a comprehensive image based on matching imaging information from the area of overlap.

14. The method of claim 11, wherein the plurality of the scanning areas are contiguous, and comprising generating the sub-image for each of the scanning areas and stitching together the sub-images into a comprehensive image based on matching imaging information from the areas near the contiguity.

15. The method of claim 11, comprising defining one or more of the scanning areas to be displaced in at least two dimensions in relation to each other, and comprising stitching together the sub-images by feature registration in at least two dimensions.

16. The method of claim 11, further comprising tuning the beam optics between cycles of scanning areas corresponding to sub-images and generating the sub-images.

17. The method of claim 11, comprising controlling the microscope to selectively scan the electron beam in a plurality of scanning areas of the specimen where one or more proteins are located, and comprising analyzing the image to determine information regarding the proteins.

18. The method of claim 11, wherein converging the electron beam comprises converging the electron beam into a longitudinally stretched beam.

19. A scanning transmission electron microscope for imaging a specimen, the microscope comprising:
an electron beam source to generate an electron beam;
beam optics to converge the electron beam into a longitudinally stretched beam;
a stage to hold a specimen in the path of the electron beam;
a beam scanner to scan the electron beam across the specimen;
a detector to detect electrons transmitted through the specimen to generate an image; and
a controller to (1) define one or more scanning areas corresponding to locations of the specimen, (2) control one or more of the beam scanner and stage to selectively scan the electron beam in the scanning areas, (3) generate a sub-image for each of the scanning areas, (4) stitch together the sub-images for the scanning areas to generate a stitched-together image, and (5) analyze the stitched-together image to determine information regarding the specimen.

20. The scanning transmission electron microscope of claim 19, wherein the controller is adapted to perform one or more of (i) drift compensation and (ii) drift distortion correction to generate the stitched-together image.

* * * * *